United States Patent
Sugita et al.

(12)

(10) Patent No.: US 7,026,474 B2
(45) Date of Patent: Apr. 11, 2006

(54) METHOD FOR PRODUCING ε-CAPROLACTAM AND METHOD FOR REACTIVATING CATALYST FOR PRODUCTION OF ε-CAPROLACTAM

(75) Inventors: Keisuke Sugita, Niihama (JP); Masaru Kitamura, Niihama (JP); Masahiro Hoshino, Niihama (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 11/055,101

(22) Filed: Feb. 11, 2005

(65) Prior Publication Data
US 2005/0182254 A1   Aug. 18, 2005

(30) Foreign Application Priority Data
Feb. 16, 2004   (JP) .............................. 2004-037795

(51) Int. Cl.
*C07D 201/04*   (2006.01)
(52) U.S. Cl. ..................................... 540/536
(58) Field of Classification Search ................ 540/536
See application file for complete search history.

(56) References Cited

FOREIGN PATENT DOCUMENTS

| DE | 100 10 189 A1 | 9/2000 |
|----|---------------|--------|
| EP | 0 494 535     | 7/1992 |
| EP | 0 494 535 A1  | 7/1992 |
| EP | 0 544 531 A1  | 6/1993 |
| EP | 0 570 136 A1  | 11/1993 |
| EP | 1 352 902 A1  | 10/2003 |

*Primary Examiner*—Bruck Kifle
(74) *Attorney, Agent, or Firm*—Birch, Stewart, Kolasch & Birch, LLP

(57) ABSTRACT

A method for producing ε-caprolactam and a method for reactivating a zeolite catalyst for the production are provided. In the reactivation step, a zeolite catalyst is allowed to contact a gas containing a carboxylic acid, water and a compound selected from ammonia and amines. In accordance with the present invention, the catalytic activities of a zeolite catalyst used for the Beckmann rearrangement reaction of cyclohexanone oxime can be effectively restored. Consequently, ε-caprolactam may be produced with a high production yield for a long period of time by reusing the catalyst by the method described above.

5 Claims, No Drawings

US 7,026,474 B2

METHOD FOR PRODUCING ε-CAPROLACTAM AND METHOD FOR REACTIVATING CATALYST FOR PRODUCTION OF ε-CAPROLACTAM

BACKGROUND OF THE INVENTION

1. Field of the Invention

The invention relates to a method for reactivating a catalyst for producing ε-caprolactam. The invention also relates to a method for producing ε-caprolactam from cyclohexanone oxime using a reactivated catalyst.

2. Description of the Related Art

One of known methods for producing ε-caprolactam is a Beckmann rearrangement reaction of cyclohexanone oxime in the presence of a zeolite catalyst. Since the activity of the catalyst slowly decreases with time during use, Japanese Patent Application Laid-Open (JP-A) No. 5-9180 has proposed to allow the used catalyst to contact ammonia for reactivating the catalyst, while JP-A No. 2003-320260 has proposed for the reactivation to allow the used catalyst to contact an aqueous solution containing a quaternary ammonium compound and/or a lower alkylamine and ammonia.

SUMMARY OF THE INVENTION

The inventors of the present invention have conducted intensive studies for developing a more excellent method for reactivating a catalyst for producing ε-caprolactam. As a result, the inventors have found that the catalytic activity of a used zeolite catalyst can be effectively restored by allowing the catalyst to contact a gas containing prescribed components, and that ε-caprolactam can be produced with a high production yield using such a reactivated catalyst. The present invention has accomplished based on the findings.

The invention provides a method for producing ε-caprolactam, which comprises the steps of allowing a used zeolite catalyst to contact a gas containing a carboxylic acid, water and a compound selected from ammonia and amines to reactivate the catalyst, and subjecting cyclohexanone oxime to the Beckman rearrangement reaction in the presence of the reactivated catalyst.

In accordance with the present invention, a zeolite catalyst used for the Beckmann rearrangement reaction of cyclohexanone oxime can be effectively restored. Consequently, ε-caprolactam may be produced with a high production yield for a long period of time by reactivating and reusing the catalyst by the method described above.

DESCRIPTION OF THE PREFERRED EMBODIMENTS

A catalyst utilized in the present invention is a zeolite catalyst, which can be used for a Beckmann rearrangement reaction of cyclohexanone oxime. The zeolite catalyst may be crystalline silica having a frame structure substantially composed of only silicon and oxygen, or may be a metallosilicate containing an element other than silicon and oxygen as elements constituting its frame structure.

Examples of the elements that may be contained in the crystalline metallosilicate other than silicon and oxygen include Be, B, Al, Ti, V, Cr, Fe, Co, Ni, Cu, Zn, Ga, Ge, Zr, Nb, Sb, La, Hf, Bi and the like. At least two of these elements may be contained together in the metallosilicate. The atomic ratio of these elements to silicon may be 5 or more, and is preferably 500 or more. The atomic ratio can be measured by an atomic absorption method and a fluorescent X-ray method.

The zeolite catalyst preferably has a pentasil structure, particularly an MFI structure. The particle size of the catalyst may be in the range of from about 0.001 mm to about 5 mm, and is preferably in the range of from about 0.01 mm to about 3 mm.

When cyclohexanone oxime is subjected to the Beckmann rearrangement reaction in the presence of a zeolite catalyst, the activity of the catalyst gradually decreases due to precipitation of carbonaceous substances and heat degradation on the catalyst, which causes the decrease of conversion of cyclohexanone oxime. Accordingly, in the present invention, the zeolite catalyst after using in the Beckman rearrangement reaction is allowed to contact a gas comprising a carboxylic acid, water (steam) and a compound selected from ammonia and an amine. The catalytic activity of the zeolite catalyst is effectively restored by such a contact treatment.

The amine that may be contained in the gas for the contact treatment may be a primary, secondary or tertiary amine of an aliphatic, alicyclic or aromatic amine, which preferably has a boiling point below the contact treatment temperature under an atmospheric pressure. Ammonia and the amine may be used in combination, if necessary. Two or more of the amines may be used in combination, if necessary.

A favorable example of the amine is represented by formula (1) below:

$$NR^1R^2R^3 \tag{1}$$

where $R^1$, $R^2$ and $R^3$, each independently, represents a hydrogen atom, or an alkyl or ally group with a carbon number of 1 to 4, with the proviso that all of them are not hydrogen atoms at the same time.

Examples of the amine represented by formula (1) include monomethylamine, monoethylamine, monopropylamine, monobutylamine, dimethylamine, diethylamine, dipropylamine, dibutylamine, trimethylamine, triethylamine, tripropylamine, tributylamine, monoallylamine, diallylamine, triallylamine and the like.

The carboxylic acid contained in the gas for the contact treatment may be a monovalent or multivalent carboxylic acid of an aliphatic, alicyclic or aromatic carboxylic acid, which also has a boiling point below the contact treatment temperature under an atmospheric pressure, like the amine has. Two or more the carboxylic acids may be used in combination, if necessary.

Examples of the carboxylic acid include formic acid, acetic acid, monochloroacetic acid, dichloroacetic acid, trichloroacetic acid, monobromoacetic acid, dibromoacetic acid, tribromoacetic acid, propionic acid, 2-chloropropionic acid, 3-chloropropionic acid, 2-bromopropionic acid, 3-bromopropionic acid, butyric acid, valeric acid, 3-methylbutanoic acid, acrylic acid, 3-butenoic acid, crotonic acid, isocrotonic acid, cyclohexane carboxylic acid, benzoic acid, salicylic acid and the like. Formic acid and acetic acid are preferable among them.

With respect to the molar ratio of the components of the gas, the amount of the carboxylic acid relative to 1 mole of the combined amount of ammonia and amine may be in the range of from about 0.05 mole to about 20 moles, and is preferably in the range of from about 0.1 mole to about 10 moles. The amount of water relative to 1 mole of the combined amount of ammonia and amine and carboxylic acid may be in the range of from about 0.05 mole to about 20 moles, and is preferably in the range of from about 0.1 mole to about 10 moles.

The gas for the contact treatment may contain one or more components other than the above-described components (i.e., a carboxylic acid, water and a compound selected from ammonia and amines), if necessary, such as nitrogen, carbon dioxide, helium and argon. The combined amount of these optional components, if any, may be in the range of about 10 moles or less, and is preferably about 5 moles or less, relative to 1 mole of the combined amount of the above-described components.

The gas for the contact treatment may be prepared, for example, by gasifying the respective components above followed by mixing them, or by mixing the respective components above in the liquid state to obtain a mixed solution thereof followed by gasifying the mixed solution. A salt of ammonia and carboxylic acid may be used as a portion or all of a starting material of the ammonia and carboxylic acid. Also, a salt of amine and carboxylic acid may be used as a portion or all of a starting material of the amine and carboxylic acid.

The contact treatment temperature may be in the range of about 100° C. to about 450° C., preferably in the range of from about 150° C. to about 300° C., and is more preferably in the range of from about 150° C. to about 250° C. The contact treatment pressure may be in the range of from about 0.005 MPa to about 0.5 MPa, preferably in the range of from about 0.005 MPa to about 0.2 MPa. The period of time for the contact treatment is not limited and is appropriately selected, and may be in the range of from about 0.05 hour to about 50 hours. The contact treatment may be conducted either in a batch-wise manner or a continuous manner. The gas for the contact treatment may be recovered and reused.

The zeolite catalyst for the contact treatment may be calcined in an oxygen-containing gas such as air, before the contact treatment. Such calcination can remove carbonaceous substances, if any, precipitated on the catalyst. The oxygen content in the oxygen-containing gas may be in the range of from about 1% to about 30% by volume, and is preferably in the range of from about 5% to about 25% by volume, and the remaining portion of the oxygen-containing gas is made up with nitrogen, argon and/or carbon dioxide. The temperature of the calcination treatment may be in the range of from about 200° C. to about 600° C. The period of time for the calcination treatment is not limited and is appropriately selected, and may be in the range of from about 0.05 hour to about 50 hours. Examples of the method for the calcination treatment available include a calcination method in the presence of an alcohol (as disclosed in JP-A No. 3-207454) and a multi-stage calcination method (as disclosed in JP-A No. 2003-236394).

The zeolite catalyst reactivated as described above can be used for the Beckmann rearrangement reaction of cyclohexanone oxime. Such reactivation and reuse of the catalyst permit ε-caprolactam to be produced in high yield over a long period of time.

The Beckmann rearrangement reaction of cyclohexanone oxime may be performed by a fluid bed method, a fixed bed method or a movable bed method, under a gas phase condition. The reaction temperature may be in the range of from about 250° C. to about 500° C., and is preferably in the range of from about 300° C. to about 450° C. The reaction pressure may be in the range of from about 0.005 MPa to about 0.5 MPa, and is preferably in the range of from about 0.005 MPa to about 0.2 MPa. The feed rate (kg/h) of cyclohexanone oxime as the starting material per 1 kg of the catalyst, or the weight hourly space velocity (WHSV) ($h^{-1}$) of cyclohexanone oxime as the starting material, may be in the range of from about 0.1 $h^{-1}$ to about 20 $h^{-1}$, and is preferably in the range of from about 0.2 $h^{-1}$ to about 10 $h^{-1}$.

Cyclohexanone oxime may be introduced, alone or together with an inert gas such as nitrogen, argon or carbon dioxide, into a reaction system. Also, cyclohexanone oxime may be introduced into a reaction system by other effective methods such as a method of co-existing with ether as disclosed in JP-A No. 2-25086; a method of co-existing with a lower alcohol as disclosed in JP-A No. 2-275850; a method of co-existing with alcohol and/or ether and water as disclosed in JP-A No. 5-201965; a method of co-existing with ammonia as disclosed in JP-A No. 5-201966; and a method of co-existing with methylamine as disclosed in JP-A No. 6-107627.

When the Beckmann rearrangement reaction is repeatedly carried out by the fluid bed method, it is preferred to conduct a method comprising the steps of: continuously or intermittently taking a portion of the catalyst out of a reactor; introducing the catalyst into a regenerator for the contact treatment as described above; and returning the catalyst to the reactor after allowing the catalyst to stay in the regenerator for a prescribed period of time.

Namely a procedure for recycling the catalyst between the reactor and regenerator is preferred in the fluid bed method, since the procedure can concomitantly carry out the reaction process and reactivation process.

When the catalyst is calcined during the reactivation process by the contact treatment, a calcination furnace is preferably placed between the reactor and regenerator, and the catalyst taken out of the reactor is transferred to the regenerator after permitting the catalyst to stay in the calcination furnace for a prescribed period of time.

When the Beckmann rearrangement reaction is repeatedly carried out by the fixed bed method, it is preferred to conduct a method comprising the steps of: supplying cyclohexanone oxime to a reactor for the reaction for a prescribed period of time; stopping the supply of cyclohexanone oxime; then supplying a contact treatment gas into the reactor to conduct a reactivation treatment of the catalyst for a prescribed period of time; stopping the supply of the gas for the reactivation; and repeating the reaction and further reactivation procedures. Such a procedure is preferred in the fixed bed method, since the reactivation treatment of the catalyst can be carried out without taking the catalyst out of the reactor.

When the catalyst is calcined during the reactivation process by the contact treatment, it is preferred that at first oxygen-containing gas is supplied into the reactor to conduct the calcination for a prescribed period of time, and thereafter the contact treatment gas is supplied into the reactor.

When the Beckmann rearrangement reaction is repeatedly carried out by the movable bed method, it is preferred to conduct the above-mentioned procedure of concomitantly applying the reaction process and reactivation process, as in the same manner as that of the fluid bed method.

When the catalyst is calcined during the reactivation process by the contact treatment, a calcination furnace is preferably placed between the reactor and regenerator, and the catalyst taken out of the reactor is transferred to the regenerator after permitting the catalyst to stay in the calcination furnace for a prescribed period of time.

In a method for separating ε-caprolactam from the reaction mixture, a reaction product gas is condensed by cooling, and the condensed product is isolated, for example, by extraction, distillation crystallization or the like.

The invention being thus described, it will be apparent that the same may be varied in many ways. Such variations are to be regarded as within the spirit and scope of the invention, and all such modifications as would be apparent to one skilled in the art are intended to be within the scope of the following claims.

The entire disclosure of the Japanese Patent Application No. 2004-37795 filed on Feb. 16, 2004 indicating specification, claims and summary, are incorporated herein by reference in their entirety.

EXAMPLES

The present invention is described in more detail by following Examples, which should not be construed as a limitation upon the scope of the present invention.

The weight hourly space velocity WHSV ($h^{-1}$) of cyclohexanone oxime was calculated by dividing the supplying rate (g/h) of cyclohexanone oxime by the weight (g) of the catalyst. The conversion of cyclohexanone oxime and selectivity to ε-caprolactam were calculated by the following equations:

Conversion (%) of cyclohexanone oxime=[(X−Y)/X]×100

Selectivity (%) to ε-caprolactam=[Z/(X−Y)]×100 wherein X is a molecular amount of supplied cyclohexanone oxime, Y is a molecular amount of unreacted cyclohexanone oxime, and Z is a molecular amount of produced ε-caprolactam.

Reference Example 1

(a) Obtaining Degradation Catalyst

Crystalline silica having a MFI structure with a particle diameter of 0.3 mm or less was used as a catalyst. A reactor containing a fluid bed of the catalyst was heated to 350° C, and vaporized cyclohexanone oxime, methanol and nitrogen were supplied into the reactor. The reaction was continued for 1 week, while a reaction product gas was discharged during the reaction. The supplying ratio of cyclohexanone oxime/methanol/nitrogen was 1 kg/1.8 kg/0.8 $m^3$, while WHSV of cyclohexanone oxime was 5 $h^{-1}$ during the reaction. A portion of the catalyst was taken out of the reactor during the reaction, and was calcined at 500° C. for a residence time of 20 hours in the air flow in a calcination furnace, followed by returning the catalyst to the reactor in order to recycle the catalyst between the reactor and calcination furnace. The degradation catalyst obtained here was used in the following Examples.

(b) Evaluation of Degradation Catalyst

A catalyst layer was formed in a quartz reactor tube with an inner diameter of 1 cm by packing the tube with the degradation catalyst above, and a space that serves as a ventilation part was provided at the inlet side from the catalyst layer. Nitrogen was allowed to circulate at a flow rate of 4.2 L/h, and the reactor tube was pre-heated at 350° C. for 1 hour. The temperature of the reactor tube was reduced to 340° C. while circulating nitrogen gas at a flow rate of 4.2 L/h, and then a mixture of cyclohexanone oxime and methanol in a weight ratio of 1/1.8 (weight ratio) was supplied to the reactor tube at a supplying speed of 8.4 g/h (WHSV of cyclohexanone oxime=8 $h^{-1}$) to conduct the Beckmann rearrangement reaction of cyclohexanone oxime. Reaction gasses were collected at 0 to 0.25 hours, 5 to 5.25 hours and 20 to 20.25 hours after the start of the reaction, and the composition of each gas was analyzed by gas chromatography. Based on the composition, conversion of cyclohexanone oxime and selectivity to ε-caprolactam were calculated. The results are shown in Table 1.

Example 1

A catalyst layer was formed in a quartz reactor tube with an inner diameter of 13 mm by packing the tube with 1.5 g of the degradation catalyst obtained in Reference Example 1 above, and a space that serves as a ventilation part was provided at the inlet side from the catalyst layer. Nitrogen was circulated at a speed of 1.4 L/h in the reactor tube, and the reactor tube was pre-heated at 200° C. for 0.5 hours. Then, a mixture of 50% by weight of an aqueous acetic acid solution, 25% by weight of an aqueous ammonia solution and tri-n-propylamine in a weight ratio of 1/1.5/0.002 (weight ratio) was supplied into the reactor tube for 5 hours at a supplying speed of 7.8 g/h, while nitrogen was circulated at a speed of 1.4 L/h and the temperature of the reactor tube was maintained at 200° C. Then, feed of the mixture was stopped, and the reaction was continued for 1 hour. The Beckmann rearrangement reaction was conducted in the same manner as in Reference Example 1 (b) using the reactivated catalyst thus obtained. The composition of each gas (obtained in the same manner as in Reference Example 1(b)) was analyzed, and based on the composition, conversion of cyclohexanone oxime and selectivity to ε-caprolactam were calculated. The results are shown in Table 1.

Example 2

The same procedure as that of the Example 1 was carried out, except that a mixture of 50% by weight of an aqueous acetic acid solution and 25% by weight of an aqueous ammonia solution in a weight ratio of 1/1.5 was used in place of the mixture of 50% by weight of the aqueous acetic acid solution, 25% by weight of the aqueous ammonia solution and tri-n-propylamine in a weight ratio of 1/1.5/0.002. Table 1 shows the conversion of cyclohexanone oxime and selectivity to ε-caprolactam.

Comparative Example 1

The same procedure as that of the Example 1 was carried out, except that 15% by weight of an aqueous ammonia solution was used in place of the mixture of 50% by weight of the aqueous acetic acid solution, 25% by weight of the aqueous ammonia solution and tri-n-propylamine in a weight ratio of 1/1.5/0.002. Table 1 shows the conversion of cyclohexanone oxime and selectivity to ε-caprolactam.

TABLE 1

| | Reaction (%)/Selectivity (%) | | |
|---|---|---|---|
| Example | 0 to 0.25 h | 5 to 5.25 h | 20 to 20.25 h |
| Reference Example 1 | 99.3/96.2 | 97.9/96.8 | 95.6/96.9 |
| Example 1 | 99.9/96.0 | 99.2/96.6 | 98.0/96.9 |
| Example 2 | 99.9/95.6 | 99.3/96.7 | 97.9/96.8 |
| Comparative Example 1 | 99.8/95.7 | 98.9/96.9 | 96.9/96.8 |

What is claimed is:

1. A method for reactivating a zeolite catalyst for producing ε-caprolactam by allowing the zeolite catalyst used for a Beckmann rearrangement reaction of cyclohexanone oxime to contact a gas containing a carboxylic acid, water and a compound selected from ammonia and amines.

2. The method according to claim 1, wherein the contact of the zeolite catalyst with the gas is conducted at a temperature of from about 100° C. to about 450° C.

3. The method according to claim 1 or 2, which further comprising the step of calcining the zeolite catalyst in an oxygen-containing gas before the step of the contact with the gas.

4. The method according to claim 3, wherein the step of calcination is conducted at a temperature of from about 200° C. to about 600° C.

5. A method for producing ε-caprolactam, which comprises the steps of:
    reactivating the catalyst for producing ε-caprolactam by the method according to claim 1 to reactivate the catalyst; and
    subjecting cyclohexanone oxime to the Beckman rearrangement reaction in the presence of the reactivated catalyst.

* * * * *